United States Patent [19]

Engel

[11] 4,323,713
[45] Apr. 6, 1982

[54] PREPARATION OF MONO-TERTIARY BUTYLHYDROQUINONE

[75] Inventor: Dusan J. Engel, Des Plaines, Ill.

[73] Assignee: UOP Inc., Des Plaines, Ill.

[21] Appl. No.: 208,952

[22] Filed: Nov. 20, 1980

[51] Int. Cl.³ .................... C07C 37/11; C07C 39/08
[52] U.S. Cl. .................................. 568/766; 568/788; 568/793; 568/785; 568/790
[58] Field of Search .............. 568/766, 788, 785, 793, 568/790

[56] References Cited

U.S. PATENT DOCUMENTS

| | | | |
|---|---|---|---|
| 2,147,256 | 2/1939 | Ipatieff | 568/790 |
| 2,722,556 | 11/1955 | Young | 568/766 |
| 2,767,230 | 10/1956 | Brown | 568/790 |

FOREIGN PATENT DOCUMENTS

| | | | |
|---|---|---|---|
| 1073638 | 6/1967 | United Kingdom | 568/766 |
| 1322909 | 7/1973 | United Kingdom | 568/766 |

*Primary Examiner*—Werren B. Lone
*Attorney, Agent, or Firm*—James R. Hoatson, Jr.; Raymond H. Nelson; William H. Page, II

[57] ABSTRACT

Hydroquinone is subjected to an alkylation reaction utilizing isobutylene or t-butyl alcohol as the alkylating agent to obtain t-butyl hydroquinone. The alkylation reaction is effected in the presence of an acidic catalyst such as phosphoric acid at temperatures ranging from about 75° to about 200° C. and a pressure in the range of from about atmospheric to about 100 atmospheres. By employing a mixture of a nonpolar hydrocarbon solvent such as xylene and an aliphatic ketone such as 2-heptanone, it is possible to obtain a greater ratio of mono-alkylated product to di-alkylated product.

11 Claims, No Drawings

PREPARATION OF MONO-TERTIARY BUTYLHYDROQUINONE

BACKGROUND OF THE INVENTION

Mono-tertiary butylhydroquinone (MTBHQ) is a compound which has been shown to possess excellent antioxidant properties with a concomitant low toxicity. The compound is utilized as an antioxidant in the food industry or as an intermediate in the preparation of other chemicals. MTBHQ is used as an antioxidant for fat, lards, oils and fat-containing food, either by incorporation into the food stuff itself or by being incorporated in the material which is used to encase or wrap the particular food stuff. In addition, the use of this compound is likely to increase in the future due to the low toxicity and higher solubility which the process relates to butylated hydroxyanisole (BHA) which heretofor has been widely used as an antioxidant in foods.

Other possible uses for this compound could include the use as a stabilizer in irradiated polypropylene, as an inhibitor for unsaturated polyester, as a stabilizer for polyethylene glycol or other polymerizable systems and to improve the color stability of gasoline antioxidants.

One method of preparing this compound is to alkylate hydroquinone with an alkylating agent such as the olefin, isobutylene; or the alcohol, t-butyl alcohol, said reaction being effected in the presence of an acidic catalyst and in a reaction medium comprising a hydrocarbon solvent. However, certain deficiencies are present in this process which renders said process difficult to effect at an acceptable economical return. For example, when utilizing a hydrocarbon solvent such as xylene for the reaction medium, an elaborate work-up section is required due to the fact that the presence of xylene with water requires azeotropic distillation followed by a number of crystallization steps to improve the purity of the final product. In addition, an object of the process is to obtain the mono-alkylated product in as great a yield as possible. Inasmuch as the amount of di-alkylated product which is formed during the reaction is present in an inordinant amount, it is necessary to separate the two compounds in order to provide an effective antioxidant compound. The separation step which may be necessary therefore entails an additional operating procedure as well as requiring additional equipment, all of which adds to the overall cost of the process, thereby reducing the return on the finished product.

As will hereinafter be shown in greater detail, it has now been discovered that, by effecting the alkylation reaction in a reaction medium of a certain type, it is possible to obtain a greater amount of mono-alkylated product while concomitantly increasing the selectivity to the desired product.

DETAILED DESCRIPTION OF THE INVENTION

This invention relates to a process for preparing tertiary butylhydroquinone. More particularly, the invention is concerned with an improvement in a process for the alkylation of hydroquinone with an alkylating agent whereby a greater amount of mono-alkylated product is produced.

As hereinbefore set forth, mono-tertiary butylhydroquinone is finding an increased use in the food industry as an additive to food stuffs to act as an antioxidant and thus prevent the deterioration, or spoilation of said food stuffs. The mono-tertiary butylhydroquinone possesses greater antioxidant properties and lower toxicity than does the corresponding di-tertiary butylhydroquinone, and therefore when preparing the antioxidant via the alkylation reaction, it is preferred that a relatively greater amount of mono-product be obtained in relation to the di-product.

It is therefore an object of this invention to provide a process for the preparation of mono-tertiary butylhydroquinone.

A further object of this invention is to provide an improvement in the process which involves the alkylation of hydroquinone with an alkylating agent whereby improved yields of the mono-alkylated product are obtained.

In one aspect, an embodiment resides in a process for the preparation of mono-tertiary butylhydroquinone which comprises reacting hydroquinone with an alkylating agent comprising isobutylene or t-butyl alcohol at reaction conditions in the presence of an acidic alkylation catalyst in a reaction medium comprising a mixture of a non-polar hydrocarbon and an aliphatic ketone, and recovering the resultant mono-tertiary butylhydroquinone.

A specific embodiment of this invention is found in a process for the preparation of mono-tertiary butylhydroquinone which comprises reacting hydroquinone with isobutylene at a temperature in the range of from about 75° to about 200° C. and a pressure in the range of from about atmospheric to about 100 atmospheres in the presence of a catalyst comprising phosphoric acid in a reaction medium comprising a mixture of xylene and 2-heptanone, and recovering the resultant mono-tertiary butylhydroquinone.

Other objects and embodiments will be found in the following further detailed description of the invention.

The present invention is concerned with a process for preparing tertiary butylhydroquinone, more specifically to a process for increasing the yield of the mono-alkylating product with respect to the di-alkylated product as a result of the alkylation reaction. It has now been discovered that by utilizing a mixture of a nonpolar hydrocarbon solvent and an aliphatic ketone which possesses a sufficient amount of carbon atoms in the chain to enhance the solubility of the hydroquinone, without significantly increasing the solubility of phosphoric acid, it is possible to obtain an increased yield of the desired product.

The alkylation process of the present invention in which hydroquinone is reacted with an alkylating agent comprising either isobutylene or t-butyl alcohol is effected by alkylation conditions which include a temperature in the range of from about 75° up to about 200° C. In the preferred embodiment of the invention, the reaction is effected at atmospheric pressure, although it is contemplated within the scope of this invention that superatmospheric pressures to about 100 atmospheres may be employed.

The superatmospheric pressures, which are afforded by the introduction of a substantially inert gas such as hydrogen, helium, argon, etc. into the reaction mixture, are employed when the alkylation reaction is effected at temperatures in the upper range of those hereinbefore set forth. The alkylation reaction utilizing the aforesaid reactants will be effected during a period which may range from about 0.5 up to about 5 hours or more in duration, the residence time being dependent upon the various reaction parameters such as temperature and pressure which are employed.

The catalyst which is utilized to effect the desired reaction will comprise an acidic alkylation catalyst and preferably a phosphoric catalyst such as phosphoric acid, pyrophosphoric acid, orthophosphoric acid, etc. While, as hereinbefore set forth, a phosphoric acid comprises the preferred catalyst, it is to be understood that the present invention is not necessarily limited to these compounds, and that other alkylation catalysts may also be employed to effect the desired reaction.

The medium in which the alkylation reaction is effected will comprise a mixture of a nonpolar hydrocarbon solvent and an aliphatic ketone. Examples of nonpolar hydrocarbon solvents which may be employed will include such compounds as aromatic hydrocarbons, and preferably alkylaromatic compounds such as toluene, o-xylene, m-xylene, p-xylene, 1,2,3-trimethylbenzene (hemimellitene), 1,2,4-trimethylbenzene (pseudocumene), 1,3,5-trimethylbenzene (mesitylene), etc.

The aforementioned hydrocarbon solvents are mixed with an aliphatic ketone which will contain from about 3 to about 8 carbon atoms in the chain. Examples of these aliphatic ketones which may be employed will include acetone, methyl ethyl ketone, 2-pentanone, 3-pentanone, 2-hexanone, 3-hexanone, 2-heptanone, 3-heptanone, 4-heptanone, 2-octanone, 3-octanone, 4-octanone, etc. While the aforementioned ketones list only the straight chain compounds, it is also contemplated within the scope of this invention that branched chain isomers of these compounds may also be employed, although not necessarily with equivalent results. The addition of these compounds to the reaction medium will increase the solubility of the hydroquinone in the reaction system to a desired point. Ketones containing 3 to 5 carbon atoms do dissolve phosphoric acid besides hydroquinone and therefore should be used only in smaller quantities, while ketones containing greater than about 8 carbon atoms are too heavy to effect the solubility of the hydroquinone and their removal in the work-up is difficult.

The addition of the aliphatic ketone to the reaction mixture will permit the recovery of a greater ratio of mono-alkylated product to di-alkylated product due to various factors. For example, the addition of this low aliphatic ketone will increase the solubility of the hydroquinone in the reaction medium and decrease the solubility of hydroquinone in phosphoric acid, thus increasing the concentration of said hydroquinone which is available for reaction with the acid catalyst and the isobutylene radical, and consequently enabling the obtention of a higher ratio of mono- to di-alkylated product. In addition, the ketone forms a protonated ketone in its enol form, which form acts as an acid itself. Due to the increase of the solubility of the hydroquinone and the formation of a protonated ketone, the necessary reaction temperature will be lowered, thus permitting a lesser amount of energy to be utilized. A further advantage of utilizing the ketone in the reaction medium lies in the fact that the solubility of the di-tertiary butylhydroquinone in the mother liquor is increased and thus a lesser amount of di-tertiary butylhydroquinone is incorporated in the product when recovering the mono-tertiary butylhydroquinone by crystallization. The amount of ketone which is present in the reaction medium will vary over a relatively wide range, said ketone being present in an amount in the range of from about 1% to about 50% by weight of the nonpolar hydrocarbon solvent, and preferably in a range of from about 10% to about 20%. Likewise, another reaction parameter is found in the amount of catalyst which is employed to effect the desired reaction.

In the preferred embodiment of the invention, the catalyst will be present in the reaction mixture in an amount in the range of from about 0.2:1 to about 0.6:1 volume of catalyst per volume of solvent, while the volume/weight ratio of solvent to hydroquinone is about 4:1. By utilizing a relatively large amount of catalyst, it is possible to effect an easier separation of the phases inasmuch as more hydroquinone is tied up in the complex; the liquid portion of the reaction mixture is less viscous and is less prompt to freeze.

The process of the present invention may be effected in any suitable manner and may comprise either a batch or continuous-type operation. For example, when a batch-type operation is employed, a quantity of the desired acidic catalyst is placed in an appropriate reaction vessel. Following this, the reaction medium comprising a mixture of a nonpolar hydrocarbon solvent such as xylene and an aliphatic ketone such as 2-heptanone is added to the apparatus and the apparatus is purged with nitrogen. Thereafter, the hydroquinone is added to the apparatus which is then heated to the desired operating temperature. Upon reaching the desired operating temperature, the alkylating agent comprising isobutylene or t-butyl alcohol is added and the flask is maintained at the desired operating temperature for a predetermined period of time. Inasmuch as the alkylation reaction is exothermic in nature, very little additional heat is required to maintain the desired temperature. Upon completion of the desired reaction time, the organic and inorganic phase are allowed to separate and are withdrawn from the reaction vessel. The organic phase may then be cooled following which the cooled phase is filtered. If so desired, after cooling and prior to filtration, the phase may be treated with a hydrocarbon solvent such as n-pentane, n-hexane, n-heptane, cyclopentane, cyclohexane, etc. and further cooled. Thereafter, the mixture is filtered and the desired product comprising mono-tertiary butylhydroquinone is separated from the di-tertiary butylhydroquinone by conventional means such as dissolution in water, filtration, distillation, etc.

It is also contemplated within the scope of this invention that mono-tertiary butylhydroquinone may also be prepared in a continuous type of operation. When this type of operation is employed, the starting materials comprising hydroquinone and an alkylating agent such as isobutylene or t-butyl alcohol are continuously charged to a reaction zone which is maintained at the proper operating conditions of temperature and pressure, the acidic catalyst of the type hereinbefore set forth also continuously charged to the reaction zone through a separate line. The reaction medium in which the alkylation is effected, comprising a mixture of a non-polar hydrocarbon solvent and an aliphatic ketone, may also be charged to the reaction zone through a separate line or, if so desired, one or both of the reactants may be mixed with the reaction medium prior to entry into said reactor, and the resulting mixture is charged thereto in a single stream. After passage through the reaction zone for a predetermined period of time, the reactant effluent is continuously withdrawn and subjected to conventional means of separation including but not limited to, cooling, filtration, extraction, distillation, etc. whereby the desired mono-tertiary butylhydroquinone may be separated from di-tertiary butylhydroquinone, unreacted starting materials, reaction medium, and catalyst, the latter three after separation being recycled to the reaction zone to form a portion of the feed stock.

The following examples are given to illustrate the process of the present invention. However, it is to be understood that these examples are given merely for purposes of illustration and that the present process is not necessarily limited thereto.

EXAMPLE I

To a three-neck, one-liter flask provided with a bottom stopcock was charged 200 ml of an 85% phosphoric acid solution. Thereafter, 400 ml of xylene was charged to the flask which was then purged with nitrogen. Following this, 100.7 grams (0.9 mole) of hydroquinone was charged thereto with stirring. The system was sealed and slowly charged with nitrogen for an additional period of about 5 minutes. The flask was then heated to 100° C. during a period of 0.5 hours while vigorously stirring the reaction mixture. After adjusting the temperature to 105° C., isobutylene was added for a period of 25 minutes until 32.0 grams (0.57 mole) had been added. During the addition of the isobutylene, very little additional heat was required to maintain the reaction temperature due to the exothermicity of said reaction. Upon completion of the reaction time, stirring was discontinued and the organic phase and aqueous phase which separated out were withdrawn and separated. The organic phase was slowly cooled to room temperature and thereafter was cooled to 10° C. utilizing ice water as the cooling agent. The organic phase was then filtered by vacuum and, in order to remove the major portion of xylene, the filter cake was dispersed in 300 cc of n-hexane, stirred for a period of 10 minutes, filtered and washed on the filter with 200 cc of cooled n-hexane. The solids were then dried at a temperature of 60° C. and high vacuum for a period of 3 hours.

To separate the mono-tertiary butylhydroquinone from the di-tertiary butylhydroquinone, the solids were placed in distilled water which had been deoxygenated by bubbling nitrogen through the water and bringing the water up to the boiling point. The mixture was magnetically stirred while 0.5% sodium dithionite was added to reduce discoloration. After allowing the boiling to proceed for a period of about 15 minutes, the mixture was filtered hot through a funnel controlled at 100° C. under suction to remove the water, and the remaining precipitate was dried in a roto evaporator at a temperature of 80° C. for a period of about 4 hours. In addition, the filtrate was also removed, slowly cooled to room temperature and then cooled to 10° C. in an ice water bath. The cooled slush was filtered, washed and dried. Analysis of the product determined that there had been a 78% molar selectivity of mono-tertiary butylhydroquinone and a 9.2% molar selectivity of di-tertiary butylhydroquinone, the weight ratio of mono-alkylated product to di-alkylated product being 6.5:1.

EXAMPLE II

A second experiment similar in nature to the one above was run utilizing an aliphatic ketone, namely 2-heptanone, as a co-solvent with the xylene. In the experiment, 200 ml of an 85% phosphoric acid solution was placed in the flask and 400 ml of a mixture comprising 80 ml of 2-heptanone and 320 ml of xylene was added thereto. The flask was slowly charged with nitrogen and 120.7 grams (1.08 mole) of hydroquinone was charged thereto while vigorously stirring the mixture. The flask was sealed and slowly charged with nitrogen for an additional period of 5 minutes. Thereafter, the temperature was raised to 105° C. with vigorous stirring during a period of 0.5 hours. When the desired temperature had been obtained, it was maintained for a period of 5 minutes to maximize the dissolution of hydroquinone. Thereafter, 30 grams (0.535 mole) of isobutylene was added during a period of 25 minutes, the temperature of the reaction being maintained at about 105° C. during this period. At the end of the addition of the isobutylene, stirring was continued for an additional period of 1 minute following which stirring was discontinued and, after separation, the organic phase and aqueous phase were withdrawn from the bottom of the flask. After separation of the two phases, the organic phase was slowly cooled to about 45° C., thereafter poured into 1600 ml of n-hexane, cooled to room temperature and, after reaching room temperature, further cooled to a temperature of 10° C. in an ice bath. After reaching this temperature, the solution was filtered, washed with an additional 250 cc of cooled n-hexane, and the precipitate was dried at a temperature in the range of from about 60° to about 80° C. under a high vacuum for 3 hours.

The separation of the mono-tertiary butylhydroquinone from di-tertiary butylhydroquinone was effected in a manner similar to that set forth in Example I above by treatment with boiling water. Gas chromatographic analysis determined that there had been a 91.8% molar selectivity of mono-tertiary butylhydroquinone and a 7.3% molar selectivity of di-tertiary butylhydroquinone, the weight ratio of mono-alkylated product to di-alkylated product being 9.5:1.

EXAMPLE III

In this example, the experiment described in Example II above was repeated by treating 120.7 grams (1.08 mole) of hydroquinone and 32.0 grams (0.571 mole) of isobutylene in the presence of 200 ml of phosphoric acid utilizing a reaction medium consisting of 200 ml of heptanone and 200 ml of xylene. The reaction conditions employed in this experiment were similar in nature to that set forth in the above example. After recovery of the alkylated product, it was determined that there had been a 93.1% molar selectivity of mono-tertiary butylhydroquinone and a 6.6% molar selectivity of di-tertiary butylhydroquinone, the weight ratio of mono-alkylated to di-alkylated product being 10.5:1.

When the alkylation reaction was effected in a reaction mixture comprising 10% 2-heptanone and 90% xylene under identical conditions, the selectivity was about 89% mono-tertiary butylhydroquinone and the mono- to di-ratio of alkylated products was about 7.9:1.

EXAMPLE IV

In a manner similar to that set forth in the above examples, hydroquinone may be subjected to an alkylation reaction with t-butyl alcohol utilizing similar reaction conditions while employing other catalysts such as pyrophosphoric acid or fluorosulfonic acid. The reaction medium in which the alkylation is effected may comprise a mixture of toluene and an aliphatic ketone such as 3-hexanone, 2-pentanone, or 3-octanone in proportions ranging from about 10 to about 50% of the aliphatic ketone. The alkylation which is effected may result in obtaining a greater ratio of mono-tertiary butylhydroquinone to di-tertiary butylhydroquinone.

I claim as my invention:

1. A process for the preparation of mono-tertiary butylhydroquinone which comprises reacting hydroquinone with an alkylating agent comprising isobutylene or t-butyl alcohol at reaction conditions in the presence of an acidic alkylation catalyst selected from the group consisting essentially of phosphoric acid and fluorosulfonic acid in a reaction medium comprising a mixture of a nonpolar hydrocarbon and an aliphatic ketone selected from the group consisting of acetone, methyl ethyl ketone, 2-pentanone, 3-pentanone, 2-hexanone, 3-hexanone, 2-heptanone, 3-heptanone, 4-heptanone, 2-octanone, 3-octanone, and 4-octanone and recovering the resultant mono-tertiary butylhydroquinone.

2. The process as set forth in claim 1 in which said reaction conditions include a temperature in the range of from about 75° to about 200° C. and a pressure in the range of from about atmospheric to about 100 atmospheres.

3. The process as set forth in claim 1 in which said acidic catalyst comprises phosphoric acid.

4. The process as set forth in claim 1 in which said acidic catalyst comprises pyrophosphoric acid.

5. The process as set forth in claim 1 in which said acidic catalyst comprises fluorosulfonic acid.

6. The process as set forth in claim 1 in which said non-polar hydrocarbon comprises xylene.

7. The process as set forth in claim 1 in which said non-polar hydrocarbon comprises toluene.

8. The process as set forth in claim 1 in which said aliphatic ketone comprises 2-heptanone.

9. The process as set forth in claim 1 in which said aliphatic ketone comprises 3-hexanone.

10. The process as set forth in claim 1 in which said aliphatic ketone comprises 2-pentanone.

11. The process as set forth in claim 1 in which said aliphatic ketone comprises 3-octanone.

* * * * *